(12) United States Patent
Reinhardt et al.

(10) Patent No.: US 8,893,887 B2
(45) Date of Patent: Nov. 25, 2014

(54) ADHESIVE DRESSING INTEGRATED PACKAGING

(75) Inventors: Jeffrey Andrew Reinhardt, LaVale, MD (US); Jonathan Yeh, Diamond Bar, CA (US); Tyler Devin Panian, Long Beach, CA (US); George Mansour, Pomona, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 13/568,013

(22) Filed: Aug. 6, 2012

(65) Prior Publication Data

US 2014/0034536 A1 Feb. 6, 2014

(51) Int. Cl.
*A61F 13/02* (2006.01)

(52) U.S. Cl.
USPC ........................................ 206/440

(58) Field of Classification Search
CPC ....... A61F 13/02; A61F 13/023; A61F 13/00; A61F 13/15
USPC ................... 206/440; 424/443, 445
See application file for complete search history.

(56) References Cited

U.S. PATENT DOCUMENTS

| | | | | |
|---|---|---|---|---|
| 3,938,659 A | * | 2/1976 | Wardwell | 206/439 |
| 4,281,650 A | * | 8/1981 | Spiegelberg | 206/440 |
| 4,781,293 A | | 11/1988 | Johns | |
| 5,040,677 A | * | 8/1991 | Tubo et al. | 206/440 |
| 5,099,832 A | | 3/1992 | Ward | |
| 5,341,922 A | * | 8/1994 | Cerwin et al. | 206/63.3 |
| 5,489,262 A | * | 2/1996 | Cartmell et al. | 602/57 |
| 5,950,830 A | * | 9/1999 | Trigger | 206/440 |
| 6,326,069 B1 | * | 12/2001 | Barnett et al. | 428/35.7 |
| 2004/0168945 A1 | * | 9/2004 | Houze | 206/440 |
| 2009/0216169 A1 | * | 8/2009 | Hansen et al. | 602/48 |
| 2011/0174651 A1 | * | 7/2011 | Kimball | 206/440 |
| 2011/0253304 A1 | | 10/2011 | Ohta | |
| 2011/0253574 A1 | * | 10/2011 | Grossman | 206/440 |

FOREIGN PATENT DOCUMENTS

DE 19916523 6/2000

OTHER PUBLICATIONS

International Search Report and Written Opinion for PCT/US2013/053055 mailed Oct. 24, 2013 in 11 pages.

* cited by examiner

*Primary Examiner* — Steven A. Reynolds
*Assistant Examiner* — King M Chu
(74) *Attorney, Agent, or Firm* — McDermott Will & Emery LLP

(57) ABSTRACT

An integrated package is disclosed that is configured for an adhesive dressing having at least one area coated with an adhesive. The integrated package includes first and second packaging elements that, when coupled together, form a sealed volume with the adhesive dressing disposed within the sealed volume. The integrated package has at least one release surface coupled to the first packaging element, wherein a first portion of the release surface is removably coupled to the adhesive of the dressing. When the adhesive dressing is removed from the integrated package, the adhesive of the dressing is exposed without requiring a second step of removing a protective sheet. The release surface may be provided as a coating on the first packaging element or as a surface of a release sheet having an edge captured between the first and second packaging elements.

15 Claims, 4 Drawing Sheets

ADHESIVE DRESSING INTEGRATED PACKAGING

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

1. Field

The present invention generally relates to sterile packaging and, in particular, packaging for adhesive surgical coverings.

2. Description of the Related Art

Adhesive dressings are commonly used to cover a wound or other break in the skin. One commonly available example is the adhesive bandage, used by almost everyone to cover cuts and scrapes, that is rectangular with a gauze pad in the middle and adhesive areas on each side. Adhesive dressings are available in a variety of sizes and configurations to allow application over a range of sizes of injury as well as to injuries located in difficult-to-cover areas such as knuckles and finger tips.

In hospitals, adhesive surgical covers are often used to protect an infusion site, i.e. the location where an infusion cannula penetrates the skin and enters a vein. As a patient may receive infusions for an extended period of time, it is important to protect the infusion site against contamination that would lead to an infection of the site. Infusion site covers often have a clear membrane with adhesive applied around the perimeter so that the infusion site itself is visible but is not in contact with the adhesive.

Adhesive covers and dressings are usually provided with one or more release sheets covering the adhesive portions to form a handleable dressing that is commonly sterile packaged between two sheets of paper that are bonded around the edge to form a sterile envelope. The handleable dressing is loose within the sterile envelope.

SUMMARY

One of the challenges of using adhesive dressings and covers, especially with the larger covers, is removing the protective sheet from the adhesive portion of the bandage without dropping the sterile cover. It commonly take two hands to open the two sheets of paper that form a conventional sterile package, and it is not uncommon for the handleable dressing to fall out as the package is being opened. A sterile dressing, for example an infusion site cover, that comes into contact with a non-sterile surface, such as clothing or bed sheets, is no longer considered sterile and is commonly discarded to avoid the risk of contaminating an infusion site. Handling adhesive covers is a particular challenge when wearing gloves, as is commonly done in hospitals when treating wounds or preparing infusion sites.

It is desirable to provide a sterile package for adhesive dressings and similar items that facilitates removal of the adhesive dressing from the package and removal of the release sheets from the adhesive portion of the cover.

In certain embodiments, an integrated package is disclosed that includes a first packaging element, an adhesive dressing comprising at least one area coated with an adhesive, and at least one release sheet coupled to the first packaging element. The at least one release sheet comprises a first surface wherein a first portion of the first surface is removably coupled to the adhesive. The integrated package also includes a second packaging element coupled to the first packaging element so as to form a sealed volume with the adhesive dressing disposed within the sealed volume.

In certain embodiments, a package is disclosed that includes a first packaging element, a second packaging element configured to be coupled to the first packaging element so as to form a sealed volume, and at least one release sheet coupled to the first packaging element so as to be within sealed volume after the second packaging element is coupled to the first packaging element. The release sheet comprises a first surface wherein a first portion of the first surface is configured to be removably coupled to an adhesive.

In certain embodiments, a method of packaging an adhesive dressing having an exposed adhesive is disclosed. The method includes the steps of coupling a first portion of a first surface of a release sheet to the adhesive of the adhesive dressing, coupling the release sheet to a first packaging element, and coupling a second packaging element to the first packaging element to form a sealed volume with the adhesive dressing disposed within the sealed volume.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1A:
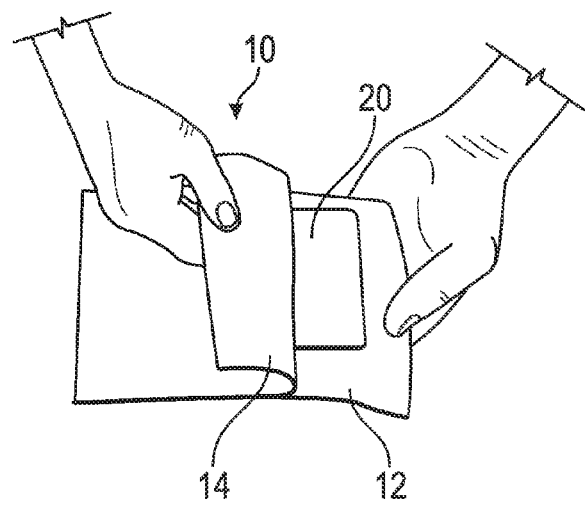
FIGS. 1A and 1B depict two steps of removing a handleable adhesive dressing from a conventional dual-layer paper sterile package.

The following description discloses embodiments of a package that integrates a protective enclosure with a release sheet that covers and protects the adhesive surfaces of the adhesive dressing, or equivalent as described above, so as to facilitate removal of the release sheet when removing the adhesive dressing from the package. In certain embodiments, this type of integrated package is suitable for use in packaging sterile dressings, as well as other medical supplies and devices, in a healthcare environment. This integrated packaging is particularly suited for use by individuals, such as doctors and nurses, wearing gloves.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

It will be apparent to those of skill in the art that the concepts and designs disclosed herein may be applied to other areas in other fields of activity. For example, the integrated package may be suitable for use with highly adhesive patches for sealing holes in tanks or pipes. While the disclosure herein is drawn to a healthcare environment, the scope of the claims are not intended to be limited to the aspects shown herein.

As used within this disclosure, the term "adhesive dressing" means any partially flexible device having at least a portion of a surface covered with an adhesive and configured to be adhered to the skin of a patient, including wound dressings, infusion site covers, infusion line securements, monitoring patches, transdermal medication delivery systems, and adhesive tape. An adhesive dressing may include a gauze pad or equivalent absorptive element. An adhesive dressing may also be configured as a protective cover that may be clear or translucent so as to allow visual inspection of the covered area. An adhesive dressing may be shaped as a rectangle or configured with tab, extended portions, or divided portions suitable for specialized applications. In some embodiments, an adhesive dressing may include electronics or medications. An adhesive dressing may have adhesive over a portion of a surface, thereby forming an adhesion area, or an entire surface.

As used within this disclosure, the term "release sheet" means a temporary covering of an adhesive area. The release sheet has at least one surface coated with a material such that an adhesive forms a bond sufficient to retain the adhesive area coupled to the release sheet in the absence of an applied force but the adhesive area will peel away from the release sheet without damage when a force is applied. The release sheet may be provided as a flexible sheet, for example a sheet of plastic such as used on a BAND-AID® or other adhesive dressing, or a coating on a rigid surface, for example a rigid tray coated with Teflon® or other non-stick coating.

As used within this disclosure, the term "formed tray" means an element having a rigid or semi-rigid shape with length and width and a depth that exceeds the thickness of the material of the formed tray. The tray may have a raised perimeter surrounding a recess with the raised perimeter configured such that a packaging element, for example a flexible sheet, may be bonded or otherwise coupled to the raised perimeter to form a sealed volume. A formed tray may have one or more than one recess and may have one or more than one sealed volume when a packaging element is coupled to the formed tray. The recesses may be additionally formed to match the shape of the enclosed item.

Figure 1B:
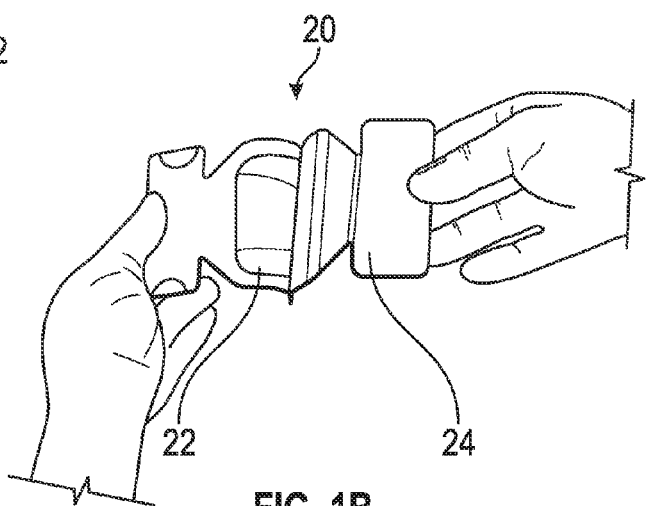

FIGS. 1A and 1B depict the two steps of removing a handleable adhesive dressing 20 from a conventional dual-layer paper sterile package 10. FIG. 1A shows the first step in which a healthcare worker opens the sterile package 10 by peeling apart the two protective layers 12 and 14. It can be seen that the handleable adhesive dressing 20, which includes an adhesive dressing 22 and a release sheet 24, is loose and unattached within the sealed volume formed by the two protective layers 12 and 14. After peeling the two protective layers 12 and 14 partially apart, the healthcare worker will remove the handleable adhesive dressing 20 from the package 10.

FIG. 1B shows the second step wherein the healthcare worker peels the release sheet 24 away from the adhesive surfaces of the adhesive dressing 22. As can be seen in FIG. 1B, the worker's left thumb is in contact with the adhesive of the adhesive dressing 22 and it is not uncommon to drop the adhesive dressing 22 at this point while trying to complete the removal of the release sheet 24 and also disengaging the adhered thumb from the adhesive dressing 22. This process is even harder to perform when wearing gloves, as the gloves may stick to the adhesive more than skin does and also allow some motion of the adhesive bandage 22 with respect to the worker's hand.

Figure 2:
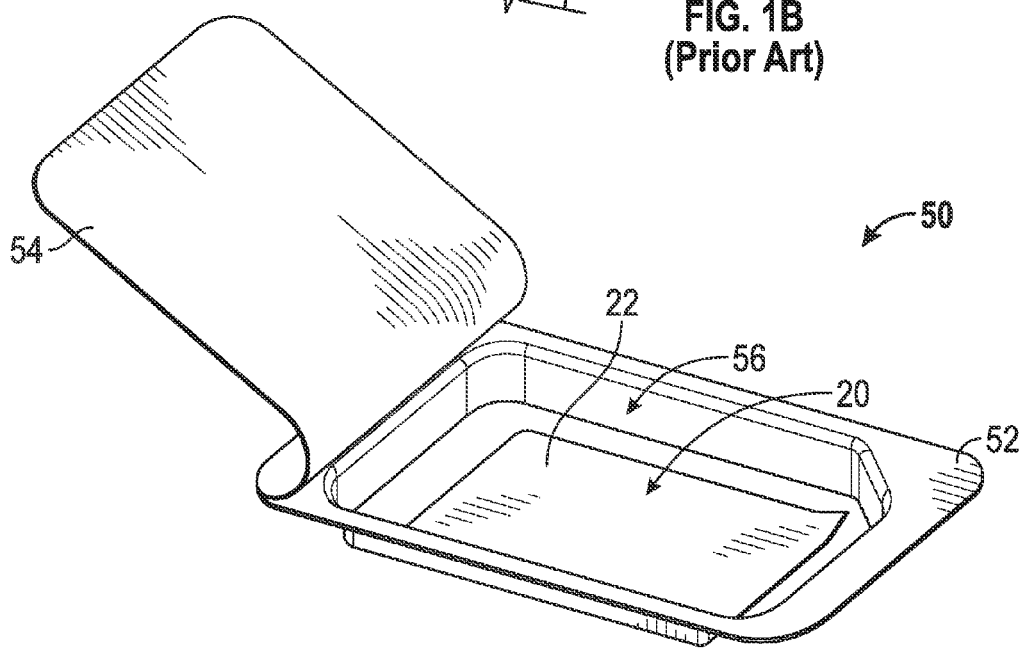
FIG. 2 depicts an exemplary integrated package according to certain aspects of the present disclosure.

FIG. 2 depicts an exemplary integrated package 50 according to certain aspects of the present disclosure. The integrated package 50 comprises a first packaging element that is, in this embodiment, a formed tray 52 with a recess 56 in which is disposed a handleable adhesive dressing 20. The integrated package 50 comprises a second packaging element that is, in this embodiment, a flexible sheet 54. The integrated package 50 comprises a release element that is, in this embodiment, a release sheet 24 that is hidden, in the view of FIG. 2, beneath the adhesive dressing 22. In certain embodiments, the release element may be a coating, a material impregnated into the material of the first packaging element, or a surface treatment applied to the material of the first packaging element. In this embodiment, the release sheet 24 is the same size as the adhesive dressing 22 with a release, or top, surface that is in contact with the adhesive areas of the adhesive dressing 22. The release sheet 24 also has a second, or bottom, surface that is coupled to the formed tray 52. The configuration of the various components and surfaces is discussed in greater detail with respect to FIGS. 3A and 3B.

In the view of FIG. 2, a second packaging element 54 has been peeled back from the formed tray 52, where the second packaging element 54 had previously been coupled to the raised perimeter of the formed tray 52 to form a sealed volume. It can be seen that once the second packaging element 54 is peeled back, the adhesive dressing 22 is still captive within the recess of the formed tray 52 and cannot accidentally fall out of the formed tray 52.

Figure 3A:
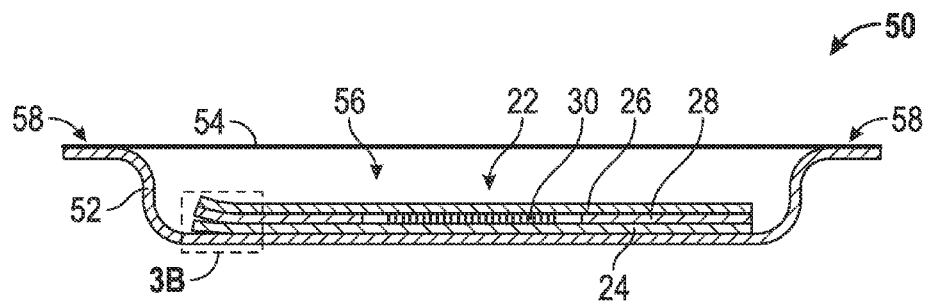
FIGS. 3A and 3B are cross-sections of the integrated package of FIG. 2 according to certain aspects of the present disclosure.
Figure 3B:
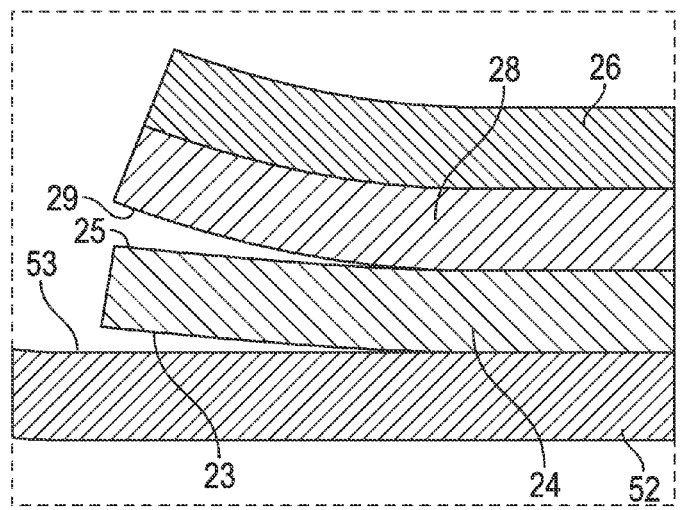

FIGS. 3A and 3B are cross-sections of the integrated package 50 of FIG. 2 according to certain aspects of the present disclosure. In this embodiment, the adhesive dressing 22 comprises an adhesive 28 coating a portion of a membrane 26, and a gauze pad 30 centrally located and coupled to the membrane 26. FIG. 3A shows a release sheet 24 coupled to the inner surface 53 (see FIG. 3B) of the formed tray 52 and the adhesive 28 coupled to the release sheet 24. In this embodiment, the gauze pad 30 is in contact with, but not adhered to, the release sheet 24. The second packaging element 54 is sealed around the perimeter 58 of the formed tray 52 to form the enclosed volume 56. The dashed line box labeled "3B" indicates the region enlarged in FIG. 3B. In certain embodiments, the thickness of the recess 56 of the formed tray 52 is greater than the total thickness of the adhesive dressing 22 and release sheet 24. In certain embodiments, the thickness of the recess 56 of the formed tray 52 is less than or equal to the total thickness of the adhesive dressing 22 and release sheet 24.

FIG. 3B is an enlarged view of the indicated portion of the adhesive dressing 22 in FIG. 3A with various elements peeled upward so as to allow better identification of certain surfaces.

In the embodiment shown in FIG. 3B, the membrane 26 and adhesive layer 28 are peeled away from the release sheet 24. The adhesive layer 28 has a surface 29 that was protected by contact with a first surface 25 of the release sheet 24. The release sheet 24 also has a second surface 23 that is coupled to the surface 53 of the formed tray 52. In certain embodiments, the release layer 24 does not peel away from the formed tray 52.

Figure 4A:
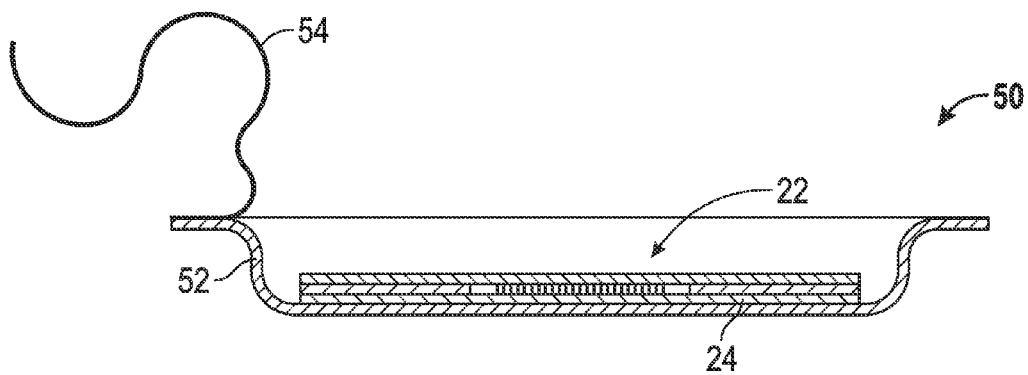
FIGS. 4A and 4B depict steps in the process of removing an adhesive dressing from the integrated package of FIG. 2 according to certain aspects of the present disclosure.
Figure 4B:
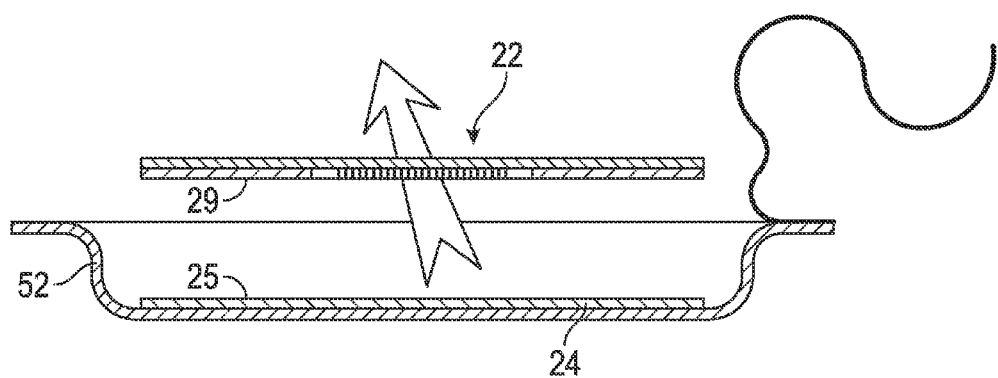

FIGS. 4A and 4B depict steps in the process of removing an adhesive dressing 22 from the integrated package 50 of FIG. 2 according to certain aspects of the present disclosure. The process may be considered to start with the configuration shown in FIG. 3A. In FIG. 4A, the second packaging element 54 has been partially peeled away from the formed tray 52, similar to the configuration shown in FIG. 2.

FIG. 4B shows the adhesive dressing 22 being removed from the formed tray 52, as indicated by the arrow, while the release sheet 24 remains coupled to the formed tray 52. This reduces the risk of dropping the adhesive dressing as the worker's hand remains in contact with the formed tray 52 and the second packaging element 54 thereby avoiding contact with the adhesive 38. The release sheet 24 protects the surface 29 of the adhesive layer 28 from contact with the air, thereby preventing the adhesive of layer 28 from drying out and losing effectiveness. In some embodiments, the attached release sheet 24 covers a first portion of the surface 29 and a second release sheet (not shown in FIG. 4B) covers a second portion of the surface 29.

Figure 5:
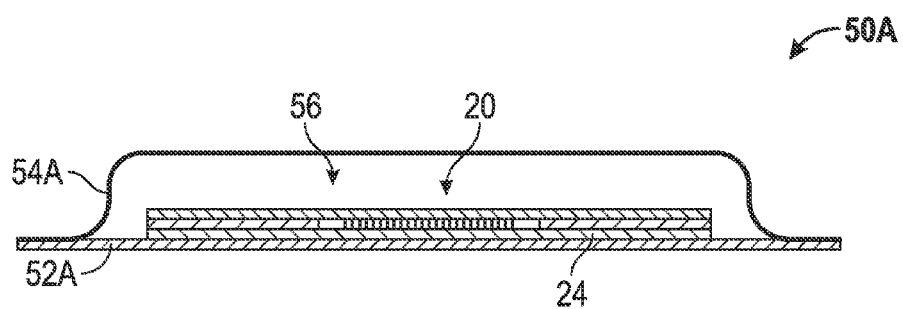
FIG. 5 is a cross-section of another embodiment of an integrated package according to certain aspects of the present disclosure.

FIG. 5 is a cross-section of another embodiment of an integrated package 50A according to certain aspects of the present disclosure. In this embodiment, the first packaging element 52A is flat and the second packaging element 54A is formed. In certain embodiments, the first packaging element 52A is flexible. In certain embodiments, the first packaging element 52A is approximately rigid. In certain embodiments, the second packaging element 54A is flexible. In certain embodiments, the second packaging element 54A is approximately rigid. In certain embodiments, the second packaging element 54A is provided as a flat sheet and forms a sealed volume 56 by wrinkling and stretching when coupled around the perimeter of the flat first packaging element 52A.

In certain embodiments, the surface 25 of release sheet 24 is provided as a release surface of a coating (not shown) applied to the surface of first packaging elements 52 or 52A. In certain embodiments, the release surface of the coating covers the entire top surface of the first packaging element 52 or 52A.

Figure 6:
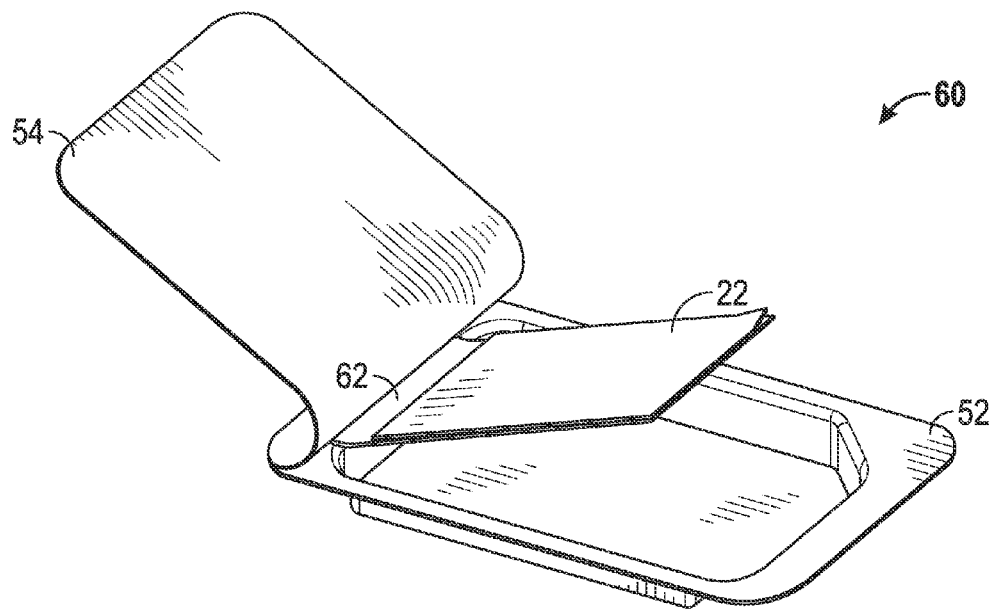
FIG. 6 depicts another embodiment of an integrated package according to certain aspects of the present disclosure.

FIG. 6 depicts another embodiment of an integrated package 60 according to certain aspects of the present disclosure. In this embodiment, the release sheet 62 extends beyond the adhesive dressing 22 and is captured and coupled between the second packaging element 54 and the formed tray 52. The non-captured portion of the release sheet 24, and the removably coupled adhesive dressing 22, are free to swing upward so as to provide easier access to the adhesive dressing 22 for removing it from the integrated package 60.

Figure 7A:
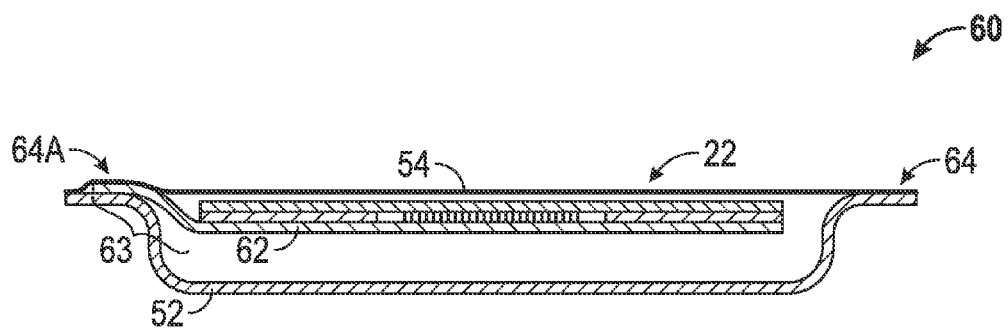
FIGS. 7A and 7B depict steps in the process of removing an adhesive dressing from the integrated package of FIG. 6 according to certain aspects of the present disclosure.
Figure 7B:
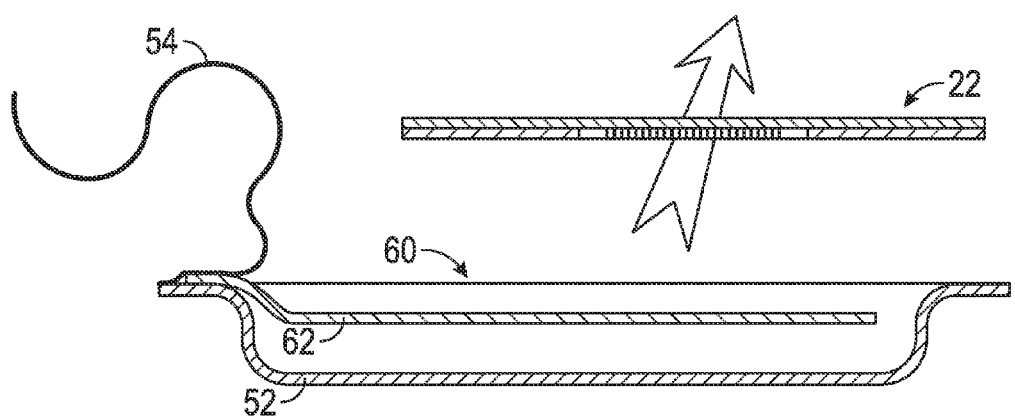

FIGS. 7A and 7B depict steps in the process of removing an adhesive dressing 22 from the integrated package 60 of FIG. 6 according to certain aspects of the present disclosure. FIG. 7A shows the sealed condition of the integrated package 60 with the second packaging element 54 sealed to the perimeter 64 of the formed tray 52. It can be seen that an extended portion 63 of the release sheet 62 is captured between the second packaging element 54 and the formed tray 52 in one portion 64A of the perimeter 64. In certain embodiments, this capturing is accomplished via mechanical means, such as stapling or thermal staking, while in other embodiments, the capture is accomplished through adhesive.

FIG. 7B shows the adhesive dressing 22 being removed from the integrated package 60, as indicated by the arrow, with the release sheet 62 remaining coupled to the formed tray 52. The ability of the release sheet 62 to move away from the formed tray 52 allows some or all of the adhesive dressing 22 to be rigid, as flexibility of the release sheet 62 facilitates peeling the rigid portion of the adhesive dressing 22 away from the release sheet 62.

The disclosed examples of an integrated package show the advantage of a release sheet that is at least partially attached to the external packaging. While the disclosed examples include a formed tray, certain embodiments also include flexible flat packaging elements similar to those of conventional packages. The attachment of the release sheet to the external package reduces the two steps of conventional packaging, shown in FIGS. 1A and 1B, to a single step that simultaneously removes the adhesive dressing from the protective packaging and removes the release sheet. This reduces the risk of dropping the adhesive dressing as well as reduces the work of the healthcare worker.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the term "some" refers to one or more.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "operation for."

Although embodiments of the present disclosure have been described and illustrated in detail, it is to be clearly understood that the same is by way of illustration and example only and is not to be taken by way of limitation, the scope of the present invention being limited only by the terms of the appended claims.

What is claimed is:

1. An integrated package comprising:
   a first packaging element;

an adhesive dressing comprising at least one area coated with an adhesive;
a release sheet comprising an extended portion and at least one release surface, the release sheet coupled to the first packaging element, wherein a first portion of the release surface is removably coupled to the adhesive, the release surface being the same size as the adhesive dressing; and
a second packaging element coupled to the first packaging element so as to form a sealed volume with the adhesive dressing disposed within the sealed volume,
wherein the extended portion is coupled between the first and second packaging elements.

2. The integrated package of claim 1, wherein the first packaging element comprises a flexible sheet.

3. The integrated package of claim 1, wherein the first packaging element comprises a formed tray.

4. The integrated package of claim 1, wherein:
the integrated package further comprises a coating applied to the first packaging element; and
the coating comprises another release surface.

5. The integrated package of claim 1, wherein:
the release sheet comprises a second surface on an opposite side to the release surface; and
at least a portion of the second surface is coupled to the first packaging element.

6. A package comprising:
a first packaging element;
a second packaging element configured to be coupled to the first packaging element so as to form a sealed volume; and
at least one release element comprising a release sheet coupled to the first packaging element so as to be within sealed volume after the second packaging element is coupled to the first packaging element, the release element comprising a release surface wherein a first portion of the release surface is configured to be removably coupled to an adhesive, the release surface configured to be at least the same size as a dressing that is to be disposed in the package,
wherein the release sheet comprises an extended portion coupled between the first and second packaging elements.

7. The integrated package of claim 6, wherein the first packaging element comprises a flexible sheet.

8. The integrated package of claim 6, wherein the first packaging element comprises a formed tray.

9. The integrated package of claim 6, wherein the release element comprises a coating.

10. The integrated package of claim 6, wherein:
the release sheet comprises a second surface on an opposite side to the release surface; and
at least a portion of the second surface is coupled to the first packaging element.

11. A method of packaging a dressing having an adhesive, the method comprising the steps of:
coupling at least one release element comprising a release sheet to a first packaging element;
configuring a release surface of the release sheet to be at least the same size as the dressing that is to be disposed in a package;
removably coupling a first portion of the release surface to the adhesive of the dressing; and
coupling a second packaging element to the first packaging element to form a sealed volume with the adhesive dressing and the release sheet disposed within the sealed volume, wherein the release sheet comprises an extended portion coupled between the first and second packaging elements.

12. The method of claim 11, wherein:
the release sheet comprises the release surface and a second surface on an opposite side from the release surface; and
the step of coupling the release sheet to the first packaging element comprises coupling at least a portion of the second surface of the release sheet to the first packaging element.

13. The method of claim 11, further comprising:
applying a coating to the first packaging element, the coating comprising another release surface.

14. The method of claim 11, wherein the first packaging element comprises a flexible sheet.

15. The method of claim 11, wherein the first packaging element comprises a formed tray.

* * * * *